United States Patent [19]

Hoerrner et al.

[11] Patent Number: 5,391,752
[45] Date of Patent: Feb. 21, 1995

[54] PROCESS FOR THE PREPARATION OF ANTIULCER AGENTS

[75] Inventors: Robert S. Hoerrner, Scotch Plains; Joel J. Friedman, East Brunswick, both of N.J.; Joseph S. Amato, Brooklyn, N.Y.; Thomas M. Liu; Ichiro Shinkai, both of Westfield, N.J.; Leonard M. Weinstock, Hilton Head, S.C.

[73] Assignee: Merck & Co., Inc., Rahway, N.J.

[21] Appl. No.: 22,804

[22] Filed: Feb. 22, 1993

Related U.S. Application Data

[63] Continuation of Ser. No. 777,873, Oct. 15, 1991, abandoned, which is a continuation-in-part of Ser. No. 764,564, Sep. 20, 1991, abandoned.

[51] Int. Cl.⁶ .......................................... C07D 401/12
[52] U.S. Cl. .................... 546/271; 546/256; 546/118; 544/58.2
[58] Field of Search .................................... 546/271

[56] References Cited

U.S. PATENT DOCUMENTS

| | | | |
|---|---|---|---|
| 4,255,431 | 3/1981 | Junggren et al. | 546/271 |
| 4,483,781 | 11/1984 | Hartman | 514/432 |
| 4,689,333 | 8/1987 | Nohara et al. | 514/338 |
| 4,808,596 | 2/1989 | Matsuishi et al. | 514/303 |
| 4,866,174 | 9/1989 | Lamsa | 544/323 |
| 5,100,913 | 3/1992 | Samreth et al. | 352/186.42 |

FOREIGN PATENT DOCUMENTS

| | | |
|---|---|---|
| 0174726 | 3/1986 | European Pat. Off. ... C07D 401/12 |
| 0240158 | 10/1987 | European Pat. Off. ... C07D 401/12 |
| 0268956 | 6/1988 | European Pat. Off. ... C07D 401/12 |
| 0298440 | 1/1989 | European Pat. Off. . |
| 0302720 | 2/1989 | European Pat. Off. ... C07D 401/12 |
| 61-178919 | 8/1986 | Japan . |

OTHER PUBLICATIONS

Kubo et al., Synthesis of 2-[[(4-Fluoro alkoxy-2-pyridyl) methyl]sulfinyl]-1H-benzimidazoles, Chem. Pharm. Bull., 38, 2853 (1990).
Meladinis et al., Synthesis and Structure of a New Chiral Oxaziridine, Zeitsch. FurNatu-forsch., Sec. B-A, 44, 1453 (1989).
P. Brougham et al., Synthesis, 1015 (1987).
A. B. Holmes et al., Synlett, 47 (1991).
S. H. Kang and W. J. Kim, Tetrahedron Lett., 30, 5915 (1989).
L. H. Klemm et al., J. Heterocyclic Chem., 27, 1537 (1990).
K. Kubo et al., Chem. Pharm. Bull, 38, 2853 (1990).
V. Meladinis et al., Zeitsch Fur Naturforsch. Sec. B-A, 44, 1453 (1989).

*Primary Examiner*—Jane T. Fan
*Attorney, Agent, or Firm*—Catherine A. Dolan; David A. Muthard; Paul D. Matukaitis

[57] ABSTRACT

Anti-ulcer agents having a methylsulfinyl bridge between a substituted pyridine moiety and a substituted benzimidazole moiety are prepared by oxidizing the corresponding compounds, having a methylthio bridge, with magnesium monoperoxyphthalate in a suitable solvent. The reaction may be run in an aromatic hydrocarbon solvent, wherein the product may crystallize out of the reaction solution and may be directly isolated by filtration.

8 Claims, No Drawings

PROCESS FOR THE PREPARATION OF ANTIULCER AGENTS

RELATED APPLICATION

This is a continuation of application Ser. No. 07/777,873, filed on Oct. 15, 1991, now abandoned which is a continuation-in-part of application Ser. No. 764,564, filed Sep. 20, 1991, now abandoned.

BACKGROUND OF THE INVENTION

Omeprazole is a known gastric proton-pump inhibitor (Merck Index II, 6800 and references cited therein). Other related compounds, all having the substituted 2-(2-pyridylmethylsulfinyl) benzimidazole or imidazopyridine structure, have been disclosed (see for example: U.S. Pat. No. 4,689,333; 4,808,596; E.P.O. Application Nos. 0 174 726, 0 240 158, 0 268 956, 0 302 720; Jap. Application Nos. H2-49774 and S61-178919; and Chem. Pharm. Bull. 38, 2853 (1990)).

Synthetic preparations of omeprazole and related compounds typically involve multistep syntheses of which the last step is the oxidation of a sulfide, for example pyrmetazole, which has the formula IIa, to the corresponding sulfoxide, for example omeprazole, which has the formula Ia.

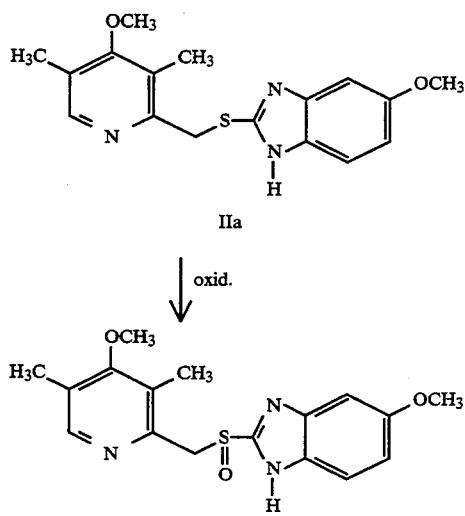

Suitable oxidizing agents previously disclosed in the art for preparing these types of compounds include peroxides, such as hydrogen peroxide, m-chloroperbenzoic acid (MCPBA), perbenzoic acid and peracetic acid (see E.P.O Application No. 0 240 158), hypohalite salts, such as sodium hypochlorite (see EP-0 268 956), iodosobenzene, 3-methyliodosobenzene (see Spanish Application No. ES540,147), and other well-known oxidizing agents (see U.S. Pat. No. 4,255,431). The most preferred oxidizing agent is usually m-chloroperbenzoic acid. Suitable solvents previously disclosed include dichloromethane, chloroform, benzene, toluene, methanol, ethanol and the like. The preferred solvent is usually dichloromethane, an enviromentally harmful halogenated solvent. All of the references noted above describe isolation of the sulfoxide by extraction into an organic solvent.

More recently E.P.O. 302 720 discloses oxidation of this type of sulfide which utilizes aqueous hydrogen peroxide in the presence of a vanadium compound which acts as a catalyst. This reference discloses that oxidation under these conditions results in higher yields of the desired sulfoxide, less N-oxide by-products and, in some cases, isolation of the product directly from the reaction mixture by filtration. Vanadium compounds are known to be highly toxic.

P. Brougham et al. (*Synthesis*, 1015 (1987)) have disclosed that magnesium monoperoxyphthalate (MMPP) is a useful oxidizing agent which may be substituted for MCPBA in a variety of oxidative synthetic applications. The main advantages which were noted are the lower cost and reduced hazard of MMPP relative to MCPBA. However, it has been disclosed that replacement of MCPBA with MMPP may provide products that are distinctly different than the products obtained when the oxidizing agent is MCPBA. (See for example: A.B. Holmes et al., *Synthetic Letters*, 47 (1991) and V. Meladinis et al., *Z. Naturforsh Sect. B, Chem Sci.* 44, 1453 (1989)). MMPP is described as being soluble in water and low-molecular-weight alcohols, but is negligibly soluble in chloroform. The use of toluene as a solvent or co-solvent in an MMPP oxidation has not been previously described.

It is the object of the instant invention to provide a novel process for the preparation of anti-ulcer agents having a methylsulfinyl bridge from the corresponding compounds having a methylthio bridge.

It is also the object of the instant invention to provide a process for the preparation of such anti-ulcer agents which utilizes an oxidizing agent which is economically improved over, substantially free from hazards associated with and free from toxic components associated with previously described oxidizing agents in analogous processes.

It is also the object of the instant invention to provide a process for the preparation of such anti-ulcer agents which utilizes a solvent system free from environmentally harmful halogenated solvents.

It is further the object of the instant invention to provide a process for the preparation of omeprazole wherein the crude omeprazole is isolated by filtration of the reaction mixture thereby eliminating the need of a more expensive and time consuming extractive isolation procedure.

SUMMARY OF THE INVENTION

The present invention provides a novel process for the preparation of a compound of the Formula I:

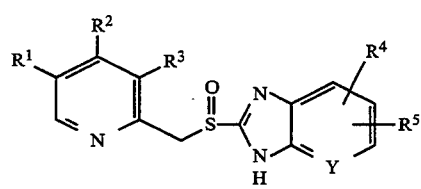

wherein
$R^1$ and $R^3$ are independently selected from:
  a) hydrogen,
  b) $C_1$–$C_8$-alkyl,
  c) $C_3$–$C_8$-cycloalkyl,
  d) $C_2$–$C_8$-floroalkyl, and
  e) $C_1$–$C_8$-alkyloxy;
$R^2$ is selected from:
  a) hydrogen,
  b) $C_1$–$C_8$-alkyl, c) $C_3$–$C_8$-cycloalkyl,
d) $C_2$–$C_8$ fluroalkyl
e) $C_1$–$C_8$ alkyloxy, and
f) —O—$(CH_2)_n$—$R^6$;

$R^4$ and $R^5$ are independently selected from:
a) hydrogen,
b) $C_1$–$C_8$-alkyl,
c) $C_3$–$C_8$-cycloalkyl,
d) —$CH_2$—$C_3$—$C_8$-cycloalkyl,
e) $C_1$–$C_8$-alkyloxy,
f) $CF_3$,
g) $C_2$–$C_8$ fluoroalkyl, and
h) —C(O)O—$C_1$–$C_8$-alkyl;

$R^6$ is selected from
a) —O—$(CH_2)_p$—$R^7$,
b) —N-pyrrolidinonyl,
c) —N-succinimidyl, d) 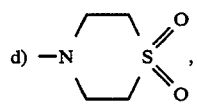

e) 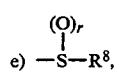

f) 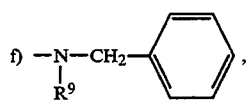

g) $OR^{10}$, h) , and i) 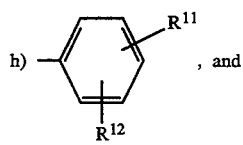;

$R^7$ is selected from:
a) hydroxy,
b) $C_1$–$C_8$-alkyloxy,
c) aryl,
d) heteroaryl,
e) —O—aryl,
f) $C_1$–$C_8$-aralkyloxy,
g) —O—$(CH_2)_s$—$OR^{10}$,
h) —halogen, and
i) —C(O)O—$R^{10}$ $R^8$ is selected from:
a) $C_1$–$C_8$-alkyl,
b) $C_3$–$C_8$-cycloalkyl,
c) $C_1$–$C_8$-aralkyl,
d) —C(O)O—$C_1$–$C_8$-alkyl,
e) pyridyl,
f) furanyl, and
g) 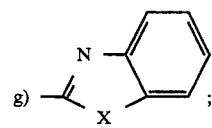;

$R^9$ is selected from:
a) acetoxy,
b) $C_1$–$C_8$ alkyl, and
c) $C_3$–$C_8$-cycloalkyl;

$R^{10}$ is selected from:
a) hydrogen,
b) $C_1$–$C_8$-alkyl, and
c) $C_3$–$C_8$-cycloalkyl, and
d) aryl;

$R^{11}$ and $R^{12}$ are independently selected from:
a) hydrogen, and
b) $C_1$–$C_8$-alkyloxy;

X is O, S, or $NR^{10}$;
Y is CH or N;
n, p and s are independently 1 to 5; and r is 0 to 2;
comprising the step of
a) treating a mixture of a compound of formula II:

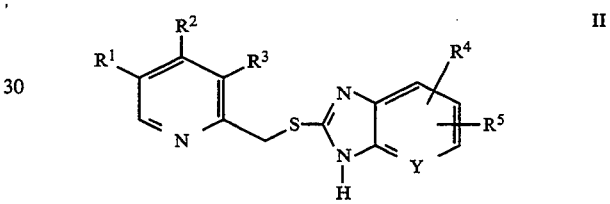

wherein the substituents $R^1$, $R^2$, $R^3$, $R^4$, $R^5$ and Y are as defined herein above, in a solvent;
with magnesium monoperoxyphthalate, in an amount sufficient to convert the compound of formula II to the compound of formula I.

The term "$C_1$–$C_8$-alkyl" includes straight and branched chain and cyclic alkyl groups having from 1 to 8 carbons. The term $C_1$–$C_8$-alkyl includes methyl, ethyl, isopropyl, propyl, butyl, sec-butyl, t-butyl, n-pentyl, and the like.

The term "$C_3$–$C_8$-cycloalkyl" includes cyclic alkyl groups having from 3 to 8 carbons. The term $C_3$–$C_8$-cycloalkyl includes cyclopropyl, cyclobutyl, cyclopentyl and the like.

The term "$C_2$–$C_8$-fluoroalkyl" includes straight and branched chain alkyl groups having from 2 to 8 carbons and having from 1 to 13 hydrogen atoms replaced by a florine atom. The term $C_2$–$C_8$-fluoroalkyl includes 2,2,2-trifluoroethyl, 2-fluoroethyl, perfluoroethyl, 2,2,3,3, tetrafluoropropyl, 2,2,3,3,4,4,4-heptafluoropentyl and the like.

The term "$C_1$–$C_8$-alkyloxy" includes straight and branched chain alkyloxy groups having from 1 to 8 carbon atoms. The term $C_1$–$C_8$-alkyloxy includes methoxy, ethoxy, n-propoxy, isopropoxy, t-butoxy, n-pentoxy and the like.

The term "aryl" includes aromatic cyclic hydrocarbons. The term aryl includes phenyl, naphthyl, phenanthrenyl and the like.

The term "heteroaryl" includes aromatic cyclic hydrocarbons wherein from 1 to 4 carbon atoms are replaced by a heteroatom selected from O, S and N. The term heteroaryl includes pyridyl, furanyl, imidazolyl, quinolinyl, indolyl and the like.

The term "$C_1$–$C_8$-aralkyloxy" includes straight and branch chain alkyl groups having from 1 to 8 carbon atoms which are substituted with an aryl group. The term $C_1$–$C_8$-aralkyloxy includes benzyloxy, 2-phenylethoxy, 2-naphthylethoxy, 3-phenylpropoxy, 2-phenyl-1-methylethoxy and the like.

The term "halogen" includes chlorine, fluorine, bromine, and iodine.

The term "mixture" includes homogeneous solution and heterogeneous mixture. The term "heterogeneous mixture" includes suspension, slurry and emulsion.

The term "solvent" includes water, water miscible solvents and water immiscible solvents and includes combinations of these solvents. The preferred solvent is a combination of water, a water miscible solvent and a water immiscible solvent.

The term "water miscible solvents" include low-molecular-weight alcohols, acetonitrile, dimethylformamide (DMF), tetrahydrofuran (THF), dioxane, methoxyethanol, tetramethylene sulfone, dimethoxyethane and the like. The preferred water miscible solvent is a low-molecular-weight alcohol.

The term "water immiscible solvent" includes benzene, toluene, xylenes, chlorobenzene, o-dichlorobenzene, chloroform, methylene chloride, cyclohexane, heptane, 2,2,4-trimethylpentane, Dowtherm and the like. The preferred water immiscible solvent is toluene.

The term "low-molecular-weight alcohol" includes hydroxy alkane compounds having 1 to 4 carbon atoms and includes branched and straight chain alcohols. The term includes methanol, ethanol, iso-propanol, butanol, isobutanol, cyclohexanol and the like. The preferred low-molecular-weight alcohol is ethanol.

The term "alkali base" includes both monobasic and dibasic salts, which include sodium carbonate, potassium carbonate, cesium carbonate, sodium bicarbonate, potassium bicarbonate, potassium phosphate, sodium phosphate and the like. The term includes aqueous solutions of such salts.

One embodiment of the process of the instant invention is that process wherein the amount of magnesium monoperoxyphthalate is 0.5. to 0.7 molar equivalents relative to the moles of pyrmetazole.

Another embodiment of the process of the instant invention is that process which further comprises an additional step of treating the mixture of the compound of formula II with an alkali base prior to the step of treating the mixture with magnesium monoperoxyphthalate.

In a class of this embodiment is the process wherein the alkali base is selected from potassium bicarbonate and sodium bicarbonate.

In a subclass of this class of the instant invention is the process wherein the amount of magnesium monoperoxyphthalate is 0.5 to 1.0 molar equivalents relative to the moles of pyrmetazole.

In another class of this embodiment is the process wherein the solvent comprises toluene.

In a subclass of this second class is the process wherein the solvent comprises toluene, a low-molecular-weight alcohol and water.

Another embodiment of the process of the instant invention is that process for the preparation of the compound omeprazole, having the formula Ia:

comprising the step of treating a mixture of the compound pyrmetazole, having the formula IIa:

in a solvent, with magnesium monoperoxyphthalate, in an amount sufficient to convert pyrmetazole to omeprazole.

In a class of this second embodiment is that process where in the solvent comprises tolune.

In a sub-class of this class is a process which further comprises the step of isolating the omeprazole from the reaction mixture by filtration.

DETAILED DESCRIPTION OF THE INVENTION

The following synthetic Scheme 1 illustrates reaction sequences in which the process of the instant invention is employed. It is understood that the scheme is meant to be illustrative and is not limiting.

SCHEME 1

The starting compound of formula II employed in the synthetic scheme are known in the art and are readily available by following the procedures described in the literature. For example, syntheses of such starting compounds are described in the followed patents and publications: U.S. Pat. Nos. 4,255,431; 4,689,333; 4,808,596; E.P.O. Application No. 0 074 341, 0 268 956, 0 302 720, 0 174 726, Spanish Appl. Nos. ES550070 and ES534275; Jap. Application Nos. H2-49774 and S61-178919; and Chem. Pharm Bull., 38, 2853 (1990).

In words relative to the equation the suitably substituted 2-(2-pyridylmethylthio)-benzimidazole II, such as 2-[[3-methyl-4-(2,2,2-trifluoroethoxy)-pyrid-2-yl]methylthio]benzimidazole; 2-[[4-(3-methoxypropoxy)-3-methylpyridin-2-yl)]methylthio]benimidazole; 2-[2-(3,5-dimethyl) pyridylmethylthio]-5-cyclopropylmethoxybenzimidazole and the like, in a suitable solvent, such as ethanol/water mixture, ethanol/toluene/water mixture and the like, is optionally treated with a suitable alkali base, such as potassium carbonate, sodium carbonate, sodium bicarbonate and the like. This solution, which may be alkaline, is then treated with magnesium monoperoxyphthalate, which may be added neat or added in a solution with a suitable solvent, such as ethanol, water, water/ethanol/toluene mixture and the like. The reaction is stirred until analytical chromatography indicates that the starting thio compound II has been converted to the sulfoxide compound I. The product may then be isolated by vacuum evaporation of the solvent followed by extractive workup or by filtration if the product precipitates out of the reaction mixture. The product may subsequently be purified by chromatography or recrystallization.

The following synthetic Scheme 2 illustrates reaction sequences in which the process of the instant invention is employed to prepare omeprazole. It is understood that the scheme is meant to be illustrative and is not limiting.

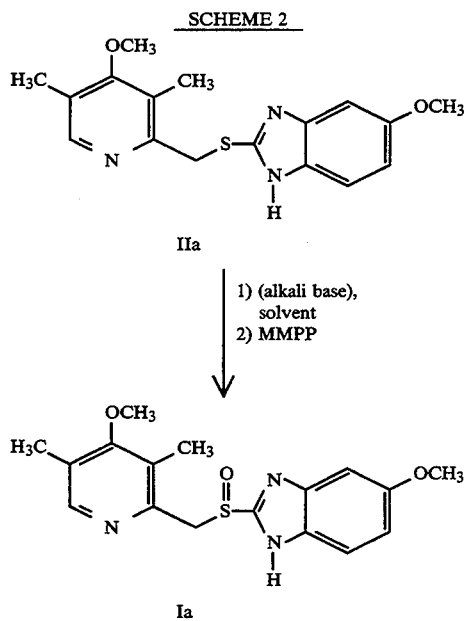

SCHEME 2

In words relative to the equation, pyrmetazole IIa in a suitable solvent, such as ethanol/water mixture, ethanol/toluene/water mixture and the like is optionally treated with a suitable alkali base, such as potassium carbonate, sodium carbonate, sodium bicarbonate and the like. The solution is then treated with magnesium monoperoxyphthalate, which may be added neat or added in a solution with a suitable solvent, such as ethanol, water, water/ethanol/toluene mixture and the like. The reaction mixture is stirred until analytical chromatography indicates that the pyrmetazole has been converted to omeprazole. The crude omeprazole may then be isolated by vacuum evaporation of the solvent followed by extractive workup. Alternatively, the product may crystallize out of the reaction mixture, especially if a suitable solvent, such as toluene/ethanol/water mixture and the like, is employed. When such crystallization occurs the crude omeprazole may be isolated by filtration.

The crude omeprazole may then be recrystallized or dissolved in strong base, decolorized and reprecipitated by reducing the pH to 9.

The invention is further defined by reference to the following examples, which are intended to be illustrative and not limiting. All temperatures are in degrees Celsius.

EXAMPLE 1

A solution of crude pyrmetazole (34.26g, 0.1041 mole) in 330 mL of 11:2; toluene/ethanol under nitrogen was treated with a solution of potassium bicarbonate (15.62 g, 0.1562 mol) in 75 mL of water and then cooled to −5° to 0° C. A solution of MMPP (37.26 g, 0.625 mol) in 150 mL of water was added dropwise to the solution over 1.5 hours while maintaining the bath temperature at between −5° to 0° C. After approximately 75% of the MMPP solution had been added the product omeprazole began to precipitate out of solution as a white solid. After the MMPP solution was completely added the reaction mixture was stirred for an additional 30 minutes. The pH of the reaction mixture was approximately 7.0 at the end of the MMPP solution addition and approximately 7.8 at the end of the additional 30 mins. The crude reaction mixture was filtered and the solid was washed with 50 mL of water and 30 mL of chilled isopropanol. The crude solid was dried under vacuum to provide 31.6 g of omeprazole (88% yield).

EXAMPLE 2

A mixture of pyrmetazole (0.112 mole) and potassium bicarbonate (0.145 mole) in 100 mL of water and approximately 250 mL of a 4:1; toluene: ethanol mixture was cooled to −5° to −9° C. with stirring. A solution of MMPP (0.67 mol) in 170 mL of water was added dropwise over a 2 hour period. After the MMPP solution was completely added a solution of sodium sulfite (2.2g) in 10 mL of water was added and the mixture was stirred for 15 minutes. The reaction mixture temperature was allowed to warm to 0° C. during this period. The slurry was then diluted with 200 mL of water and 50 mL of methanol and the pH of the slurry was adjusted to 9.1 by addition of 50% aqueous sodium hydroxide. The slurry was aged at 0° to 5° C. for 1 hour and then was filtered. The solid was washed with 50 mL of water and 40 mL cold methanol. Drying of the solid provided 31.3 g of crude omeprazole (81% yield).

EXAMPLE 3

To a solution of 3.44 g of pyrmetazole (10.5 mmol) in 30 mL of 9:1 v/v methanol/water at −10° C. was added dropwise a solution of 3.10 g of MMPP in 30 mL of 9:1 v/v methanol/water over a 10 minute period. The reaction mixture was stirred at −10° C. for 35 minutes then poured into a mixture of 100 mL of saturated aqueous sodium bicarbonate and 40 mL of methylene chloride. The layers were separated and the aqueous layer was extracted 3 times with methylene chloride. The combined organic layers were dried over anhydrous magnesium sulfate and filtered. The filtrate was concentrated under vacuum and the residue was slurried in EtOAc and the slurry stirred for 10 minutes. The solid was collected and then dried to provide 3.31 g of omeprazole (92% yield). LC analysis showed that the product was 99.5% pure.

EXAMPLE 4

A mixture of pyrmetazOle (0.108 mole) and potassium bicarbonate (0.13 moles) in 115 mL of water and 180 mL of methylene chloride was cooled to 0° C. to 4° C. while being stirred. A solution of MCPBA (0.108 moles, 72% pure) in 51 mL of methylene chloride and 13.3 mL of ethanol was added dropwise over 3 hours while the temperature was maintained between 2° to 4° C. After the addition was complete the reaction mixture was stirred an additional 0.5 hour and analyzed by HPLC to ascertain the extent of conversion. The reaction mixture was then diluted with 115 mL of cold water, and the pH was adjusted to 13-13.5 with approximately 15 mL of 50% aqueous sodium hydroxide (NaOH) while the reaction temperature was maintained between 2° to 5° C. The reaction mixture was then stirred an additional 15 minutes and the layers were separated. The organic layer was extracted with pH 13.5 NaOH in water. The basic aqueous phases were combined and treated with approximately 12 mL of methyl formate which was added over a 4 hour period. When the reaction mixture pH reached approximately 10.8, the reaction mixture was seeded with omeprazole. When the methylformate addition was complete the product was collected by filtration and rinsed with water and methanol. Drying provided 32.2 g of crude omeprazole (86% yield).

What is claimed is:

1. A process for the preparation of omeprazole, having the formula Ia:

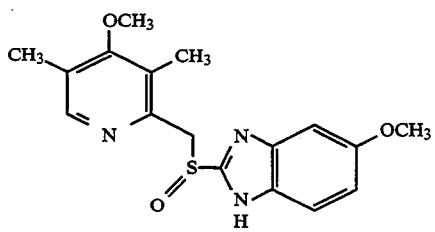

which comprises the step of treating the mixture of pyrmetazole, having the formula IIa:

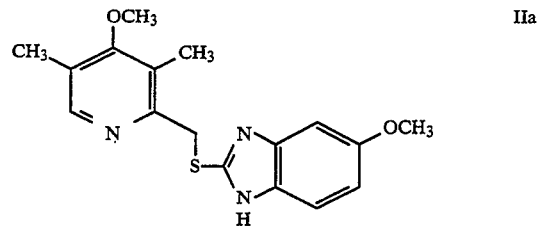

in a solvent;
cooled to 0° C. or below with magnesium monoperoxyphthalate, in an amount sufficient to convert pyrmetazole to omeprazole.

2. A process for the preparation of omeprazole, having the formula Ia:

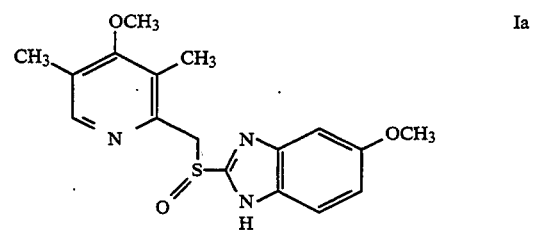

which comprises the steps of:
a) treating the mixture of pyrmetazole, having the formula IIa:

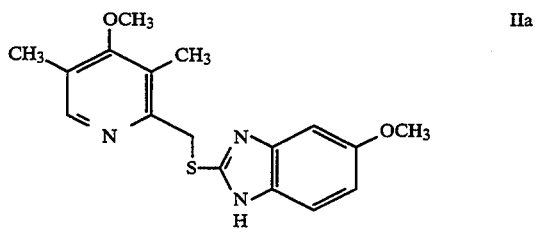

in a solvent cooled to 0° C. or below, which comprises toluene;
with magnesium monoperoxyphthalate, in an amount sufficient to convert pyrmetazole to omeprazole; and
b) isolating the compound omeprazole by filtration.

3. The process of claim 1 wherein the solvent comprises toluene.

4. The process of claim 3 wherein the solvent comprises toluene, a low molecular weight alcohol and water.

5. The process of claim 3 which further comprises the step of isolating the compound omeprazole by filtration.

6. The process of claim 1 which further comprises a step of treating the mixture of pyrmetazole with an alkali base prior to the step of treating the mixture with magnesium monoperoxyphthalate.

7. The process of claim 6 wherein the alkali base is selected from potassium bicarbonate and sodium bicarbonate.

8. The process of claim 6 which further comprises the step of isolating the compound omeprazole by filtration.

* * * * *